(12) United States Patent
Wouters et al.

(10) Patent No.: US 12,007,052 B2
(45) Date of Patent: Jun. 11, 2024

(54) BRACKETS AND METHODS OF MANUFACTURE AND USE THEREOF

(71) Applicant: DiversiTech Corporation, Duluth, GA (US)

(72) Inventors: Thomas Wouters, Duluth, GA (US); Dale Harrison, Duluth, GA (US); Chris Willette, Duluth, GA (US)

(73) Assignee: DiversiTech Corporation, Duluth, GA (US)

( * ) Notice: Subject to any disclaimer, the term of this patent is extended or adjusted under 35 U.S.C. 154(b) by 0 days.

(21) Appl. No.: 18/098,640

(22) Filed: Jan. 18, 2023

(65) Prior Publication Data

US 2023/0228348 A1    Jul. 20, 2023

Related U.S. Application Data

(63) Continuation-in-part of application No. 17/300,323, filed on Jan. 19, 2022, and a continuation-in-part of application No. 17/300,324, filed on Jul. 15, 2022.

(51) Int. Cl.
*F16L 3/00* (2006.01)
*F16L 3/237* (2006.01)

(52) U.S. Cl.
CPC .................................. *F16L 3/237* (2013.01)

(58) Field of Classification Search
None
See application file for complete search history.

(56) References Cited

U.S. PATENT DOCUMENTS

| | | | | | |
|---|---|---|---|---|---|
| 1,585,840 | A | * | 5/1926 | Fahnestock | H01R 4/48455 |
| | | | | | 439/828 |
| 2,166,916 | A | * | 7/1939 | Lombard | F16B 5/0685 |
| | | | | | 248/222.12 |
| 3,363,864 | A | * | 1/1968 | Olgreen | F16L 3/223 |
| | | | | | 248/912 |
| 5,067,677 | A | * | 11/1991 | Miceli | H02G 3/26 |
| | | | | | D8/356 |
| 5,538,210 | A | * | 7/1996 | Ohmori | F16L 3/13 |
| | | | | | 248/222.12 |
| 7,131,170 | B2 | * | 11/2006 | Weaver | A46B 17/02 |
| | | | | | 248/316.7 |
| 8,272,613 | B2 | * | 9/2012 | Golle | F16B 5/0657 |
| | | | | | 248/74.1 |
| 2023/0228347 | A1 | * | 7/2023 | Wouters | H02G 3/32 |
| | | | | | 248/74.2 |

OTHER PUBLICATIONS

Fresh-Aire UV, Airborne Duct Kit Installation Guide (2 pages).
Fresh-Aire UV, Commercial Series Accessories (1 page).
Fresh-Aire UV, Ice UV Mini Installation Guide (2 pages).
Fresh-Aire UV, Standard UV System, Installation & Maintenance of the Fresh-Aire UV Standard UV Light Kit for Commercial Air Handler Systems (5 pages).
Fresh-Aire UV, TRS-X Kit, Installation Guide (2 pages).

* cited by examiner

*Primary Examiner* — Steven M Marsh
(74) *Attorney, Agent, or Firm* — Dentons US LLP

(57) ABSTRACT

This disclosure enables various brackets and methods of manufacture and use thereof. For example, a bracket may have a first plate, a second plate, and a clip cantileveredly extending from the second plate or monolithic with the second plate.

39 Claims, 13 Drawing Sheets

BRACKETS AND METHODS OF MANUFACTURE AND USE THEREOF

CROSS-REFERENCE TO RELATED PATENT APPLICATIONS

This patent application is a continuation-in-part of U.S. non-provisional patent application Ser. No. 17/300,324 filed 19 Jan. 2022, which is incorporated by reference herein for all purposes.

This patent application is a continuation-in-part of U.S. non-provisional patent application Ser. No. 17/300,323 filed 15 Jul. 2022, which is incorporated by reference herein for all purposes.

TECHNICAL FIELD

This disclosure relates to brackets.

BACKGROUND

FIG. 1 to FIG. 2 show an assembly 100 having a bracket, a clip, a bolt, and a nut, where the clip is fastened to the bracket via the bolt and the nut. The assembly 100 may be used within an air handling unit, where the bracket may be fastened to the air handling unit and the clip may hold an ultraviolet (UV) bulb to enable a germicidal irradiation within the air handling unit. Therefore, although the assembly 100 may sometimes be useful, the assembly 100 still suffers from various technological drawbacks. First, the assembly 100 has the clip fastened to the bracket, which may be time-consuming or laborious to do, especially onsite. Second, the assembly 100 includes the bracket, the clip, the bolt, and the nut, which may be excessive, costly, or subject to supply shortages. Third, the assembly 100 is limited to specific installation scenarios within the air handling unit. Fourth, the bolt or the nut may become loosened over time, thereby causing the clip to move or become unsecured relative to the bracket. Fifth, the assembly 100 is not structurally adjustable based on where the assembly 100 is used.

SUMMARY

Generally, this disclosure enables various brackets and methods of manufacture and use thereof. These brackets address at least some of the various drawbacks noted above. For example, a bracket may have a first plate, a second plate, and a clip cantileveredly extending from the second plate or monolithic with the second plate.

There may be a device, comprising: a bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane such that the clip is able to hold a tubular member when the tubular member extends between the first finger and the second finger.

There may be a method, comprising: sending a bracket to a user, wherein the bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane; and instructing the user to operate the clip such that the clip holds a tubular member as the tubular member extends between the first finger and the second finger.

There may be a method, comprising: causing a bracket to be accessed, wherein the bracket includes a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane; and causing the clip to hold a tubular member as the tubular member extends between the first finger and the second finger.

There may be a method, comprising: manufacturing a bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane such that the clip is able to hold a tubular member when the tubular member extends between the first finger and the second finger.

DETAILED DESCRIPTION

Figure 1:
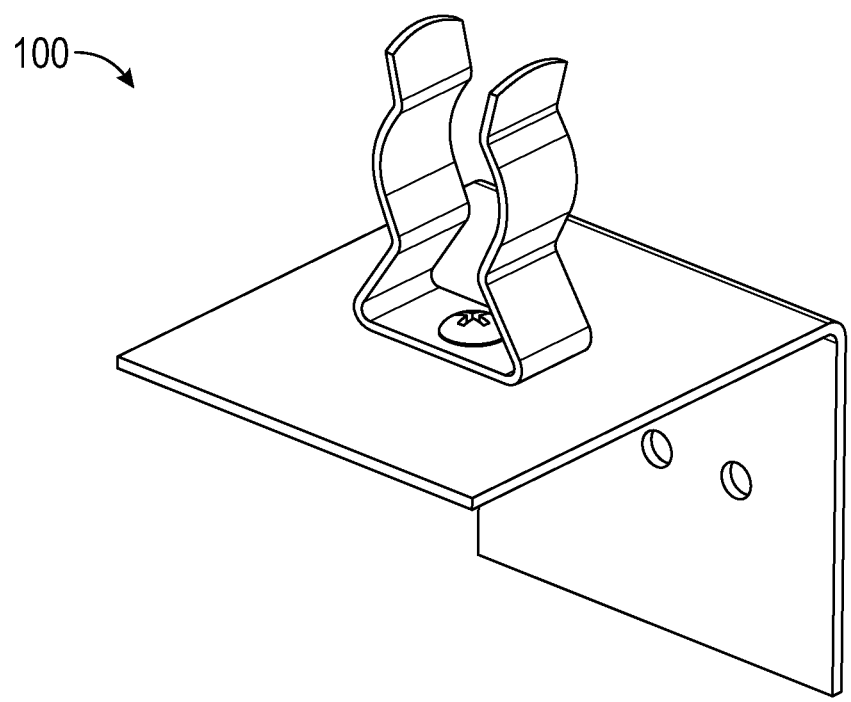
FIG. 1 shows an assembly having a bracket, a clip, a bolt, and a nut, where the clip is fastened to the bracket via the bolt and the nut.
Figure 2:
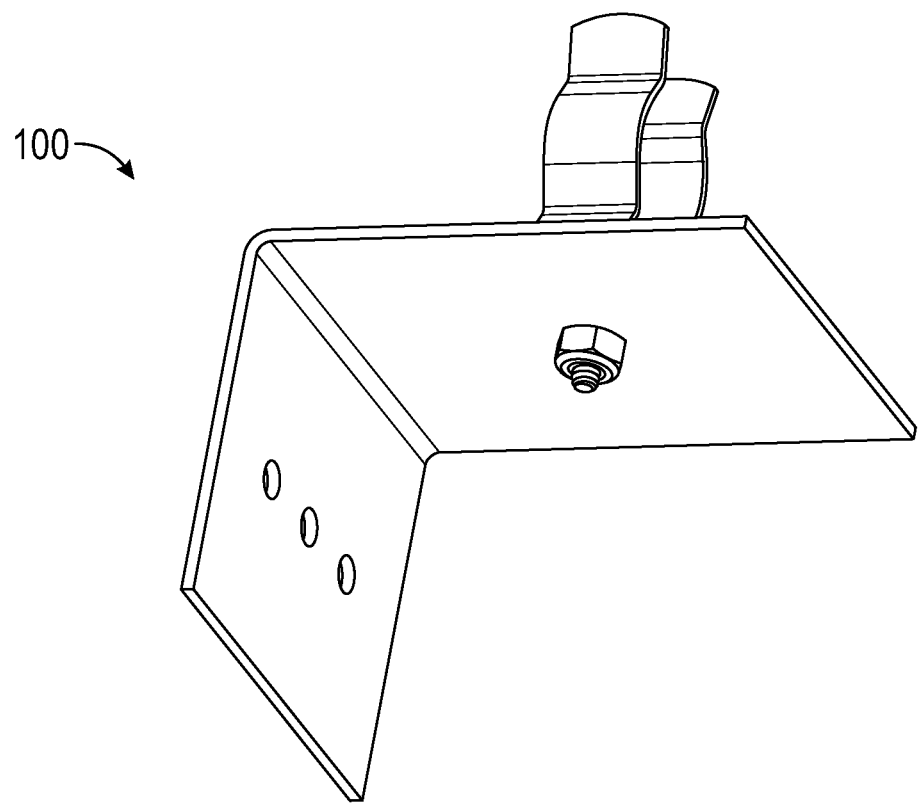
FIG. 2 shows an assembly having a bracket, a clip, a bolt, and a nut, where the clip is fastened to the bracket via the bolt and the nut.

Generally, this disclosure enables various brackets and methods of manufacture and use thereof. These brackets address at least some of the various drawbacks noted above. For example, a bracket may have a first plate, a second plate, and a clip cantileveredly extending from the second plate or monolithic with the second plate. However, note that this disclosure may be embodied in many different forms and should not be construed as necessarily being limited to various embodiments disclosed herein. Rather, these embodiments are provided so that this disclosure is thorough and complete, and fully conveys various concepts of this disclosure to skilled artisans.

Various terminology used herein can imply direct or indirect, full or partial, temporary or permanent, action or inaction. For example, when an element is referred to as being "on," "connected," or "coupled" to another element, then the element can be directly on, connected, or coupled to another element or intervening elements can be present, including indirect or direct variants. In contrast, when an element is referred to as being "directly connected" or "directly coupled" to another element, then there are no intervening elements present.

Various singular forms "a," "an" and "the" are intended to include various plural forms (e.g., two, three, four, five, six, seven, eight, nine, ten, tens, hundreds, thousands) as well, unless specific context clearly indicates otherwise.

Various presence verbs "comprises," "includes" or "comprising," "including" when used in this specification, specify a presence of stated features, integers, steps, operations, elements, or components, but do not preclude the presence or addition of one or more other features, integers, steps, operations, elements, components, or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "or others," "combination", "combinatory," or "combinations thereof" or another conceptually similar terminology refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. Skilled artisans understand that typically there is no limit on number of items or terms in any combination, unless otherwise contextually apparent.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized or overly formal sense, unless expressly so defined herein.

Relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" or "substantially" refers to a +/−10% variation from a nominal value/term. Such variation is always included in any given value/term provided herein, whether or not such variation is specifically referred thereto.

Although the terms first, second, can be used herein to describe various elements, components, regions, layers, or sections, these elements, components, regions, layers, or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Features described with respect to certain example embodiments can be combined and sub-combined in or with various other example embodiments. Also, different aspects or elements of example embodiments, as disclosed herein, can be combined and sub-combined in a similar manner as well. Further, some example embodiments, whether individually or collectively, can be components of a larger system, wherein other procedures can take precedence over or otherwise modify their application. Additionally, a number of steps can be required before, after, or concurrently with example embodiments, as disclosed herein. Note that any or all methods or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques or tolerances, are to be expected. Thus, various example embodiments of this disclosure should not be construed as necessarily limited to various particular shapes of regions illustrated herein, but are to include deviations in shapes that result, for example, from manufacturing.

Any or all elements, as disclosed herein, can be formed from a same, structurally continuous piece, such as being unitary, or be separately manufactured or connected, such as being an assembly or modules. Any or all elements, as disclosed herein, can be manufactured via any manufacturing processes, whether additive manufacturing, subtractive manufacturing, or other any other types of manufacturing. For example, some manufacturing processes include three dimensional (3D) printing, laser cutting, computer numerical control routing, milling, pressing, stamping, vacuum forming, hydroforming, injection molding, lithography, chiseling, and so forth.

Hereby, all issued patents, published patent applications, and non-patent publications that are mentioned or referred to in this specification are herein incorporated by reference in their entirety for all purposes, to a same extent as if each individual issued patent, published patent application, or non-patent publication were specifically and individually indicated to be incorporated by reference. To be even more clear, all incorporations by reference specifically include those incorporated publications as if those specific publications are copied and pasted herein, as if originally included in this disclosure for all purposes of this disclosure. Therefore, any reference to something being disclosed herein includes all subject matter incorporated by reference, as explained above. However, if any disclosures are incorporated herein by reference and such disclosures conflict in part or in whole with this disclosure, then to an extent of the conflict or broader disclosure or broader definition of terms, this disclosure controls. If such disclosures conflict in part or in whole with one another, then to an extent of conflict, the later-dated disclosure controls.

FIG. 3 to FIG. 9 show an embodiment of a bracket according to this disclosure. In particular, a bracket 200 includes a first plate 202, a second plate 204, and a clip 206. The clip 206 includes a base 210, a first finger 212, and a second finger 212.

The first plate 202 includes a metal (e.g., iron, copper, aluminum, titanium), but can include other suitable materials (e.g., alloy, plastic, rubber, wood), whether additional or alternative. The second plate 204 includes a metal (e.g., iron, copper, aluminum, titanium), but can include other suitable materials (e.g., alloy, plastic, rubber, wood), whether additional or alternative, whether identical or not identical to the first plate 202. The clip 206, including the base 210, the first finger 212, or the second finger 212, includes a metal (e.g., iron, copper, aluminum, titanium), but can include other suitable materials (e.g., alloy, plastic, rubber, wood), whether additional or alternative, whether identical or not identical to the first plate 202 or the second plate 204.

The first plate 202 is monolithic with the second plate 204, but can be assembled (e.g., fastening, mating, adhering, magnetizing) therewith. The second plate 204 is monolithic with the clip 206, including the base 210, but can be assembled (e.g., fastening, mating, adhering, magnetizing) therewith. The first finger 212 or the second finger 212 is monolithic with the base 210, but can be assembled (e.g., fastening, mating, adhering, magnetizing) therewith. For example, the base 210 can be monolithic with the second plate 204. Likewise, for example, the second plate 204 can be monolithic with the first plate 202.

As shown in FIG. 3 to FIG. 7, the first plate 202 extends along a first plane, which may be a vertical plane, and the second plate 204 extends (e.g., cantileveredly) from the first plate 202 along a second plane, which may be a horizontal plane, away from the first plane. The first plane may intersect the second plane, which can result in a perpendicular orientation (e.g., about 90 degrees), although other suitable orientations are possible (e.g., about 30 degrees, about 45 degrees, about 60 degrees, about 120 degrees, 150 degrees). For example, the first plane and the second plane may intersect at an angle of about 90 degrees. As such, the second plate 204 may extend from the first plate 202 such that the first plate 202 and the second plate 204 collectively form an L-shape, although other shapes are possible, whether additional or alternative. For example, the second plate 204 may extend from the first plate 202 such that the first plate 202 and the second plate 204 may collectively form an T-shape, a Y-shape, or another suitable shape. For example, the first plate 202 and the second plate 204 can be arranged as in the bracket 100 shown in FIG. 1.

Figure 3:
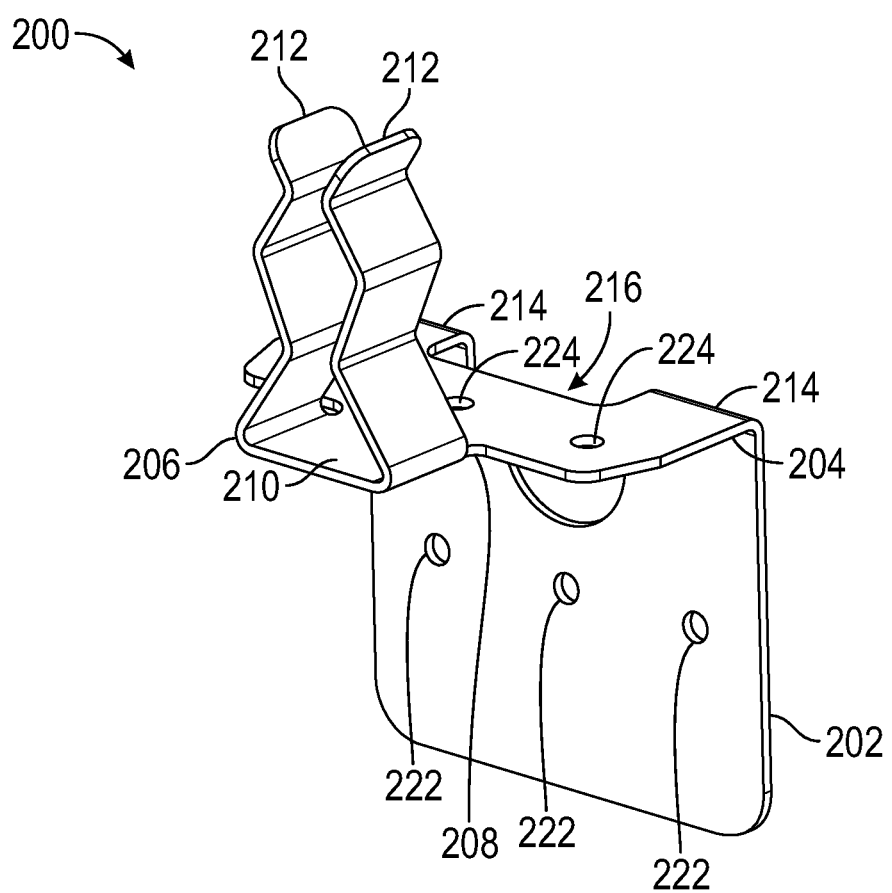
FIG. 3 to FIG. 9 show an embodiment of a bracket according to this disclosure.
Figure 6:
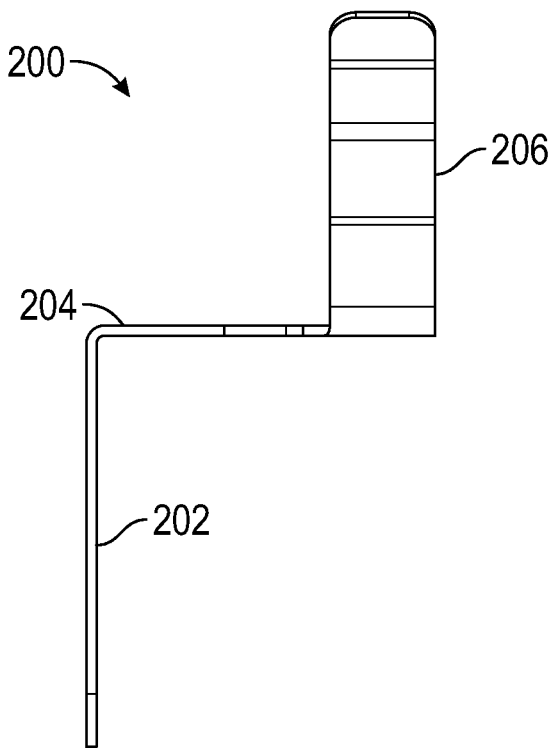
Figure 7:
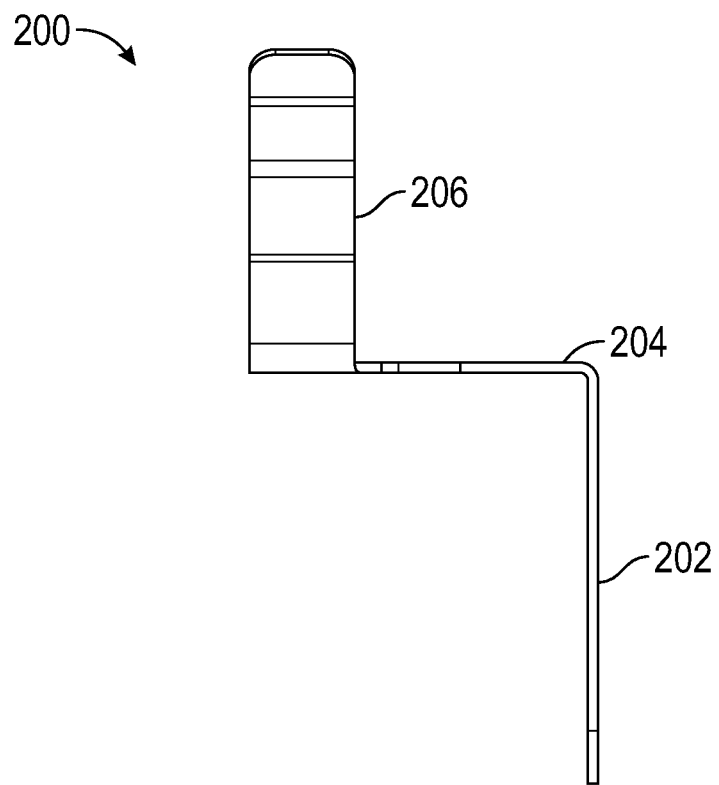

The second plate 204 includes an end section 208 distal to the first plate 202. The second plate 204, along the end section 208, is wider than the base 210, although this configuration is not required (e.g., same width or smaller width). The second plate 202 or the end section 208 transitions to the base 210 (e.g., without projections, depressions, or gaps) such that the second plate 204 is flush with the base 210, although this configuration is not required and the second plate 204 may be non-flush with the base 210 (e.g., with projections, depressions, or gaps). For example, the first plate 202, the second plate 204, and the base 210 define an L-shape, as shown in FIGS. 3, 6, and 7.

The base 210 extends (e.g., cantileveredly) from the end section 208 along the second plane, away from the first plane, which may be parallel to the second plane, although this is not required. The first finger 212 and the second finger 212 extend from the base 210 away from the second plane such that the clip 206 is able to hold (e.g., clamp) a tubular member (e.g., a tube, a shaft, a bulb) when the tubular member extends between the first finger 212 and the second finger 212, as shown in FIG. 12 to FIG. 19. For example, the first finger 212 and the second finger 212 can extend from the base 210 away from the second plane, such that the clip 206 is able to hold the tubular member when the tubular member extends between the first finger 212 and the second finger 212 and not past the first plate 202 or the first plane, as shown in FIGS. 12, 13A-14B, and 19. However, this configuration is not required. Resultantly, as shown in FIGS. 12 and 15A-16B, the first finger 212 and the second finger 212 can extend from the base 210 away from the second plane such that the clip 206 is able to hold the tubular member when the tubular member extends between the first finger 212 and the second finger 212 and past the first plate 202 or the first plane. For example, the bulb may include a gas-discharge bulb, a fluorescent bulb, or any other suitable bulb. For example, the tube may include a conduit for conveying a fluid (e.g., a liquid, a gas), a solid beam, or another suitable tubular member.

The clip 206 includes the base 210, the first finger 212 and the second finger 212, where at least one finger 212 may be longitudinally rectilinear, non-rectilinear, zigzag, arcuate, concave, convex, or another suitable shape, and where each finger has a tip portion at which such longitudinal extension terminates. For example, the clip 206, including the base, the first finger 212, or the second finger 212, can be arranged as in the bracket 100 shown in FIG. 1. The base 210 has a top side, a bottom side, and a set of sidewalls opposing each other and spanning between the top side and the bottom side, to allow that base 210 to be internally solid, although the base 210 can be internally hollow. Although the base 210 is shaped to be substantially rectangular, this form of shaping is not required. For example, base 210 may be substantially square, oval, circular, triangular, polygonal, pentagonal, hexagonal, semi of any of foregoing, or any other suitable shape. Each of the top side, the bottom side, and the pair of sidewalls is flat and smooth, but does not need to be. For example, at least one of the top side, the bottom side, or one sidewall of the pair of sidewalls may be concave, convex, sinusoidal, rough, perforated, knurled, textured, or any other suitable configuration.

Although the first finger 212 or the second finger 212 longitudinally extend in a zigzag manner while extending from the top side of the base 210, this configuration is not required. For example, the first finger 212 or the second finger 212 can longitudinally extend in a non-zigzag manner (e.g., arcuate, sinusoidal, rectilinear). Likewise, although the first finger 212 or the second finger 212 appears to complement or mirror its opposing finger, this configuration is not required. For example, one finger 212 can longitudinally extend in the zigzag manner and another finger 212 can longitudinally extend in the non-zigzag manner. Note that this differencing is not only applicable to longitudinal extension of fingers 212, but may be applicable to other parameters (e.g., width, thickness) characteristics, materials, structure, orientations, shapes, sizes, degrees of stiffness or flexibility or resiliency, or other suitable attributes. For example, one finger 212 can be more stiff or resilient than another finger 212. Note that the first finger 212 or the second finger 212 may be shaped as in the bracket 100 shown in FIG. 1, regardless of how a respective tip portion of a respective finger 212 is oriented (e.g., perpendicular, acute, obtuse) relative to the base 210. For example, the first finger 212 or the second finger 212 may have a different longitudinal extension (or another characteristic), where the different longitudinal extension can be length, shape, size, or another property.

As shown in FIGS. 3, 8, 9, and 11, the second plate 204 includes a first end portion 214 and a second end portion 214, spaced apart from each other, to collectively form an air gap 216 therebetween, such that the second plate 204 has an open shape (e.g., a U-shape, a C-shape, a V-shape) thereby, as viewed from above, when the first end portion 214 and the second end portion 214 extend (e.g., cantileveredly) from the first plate 202 along the second plane, which may be away from the first plane. For example, the second plate 204 and the base 210 may collectively form a Y-shape or another suitable open-shape, as viewed from above, as shown in FIGS. 3, 8, 9, and 11. However, note that the second plate 204 can be shaped to avoid the first end portion 214 or the second end portion 214, and thereby collectively avoiding the air gap 216. For example, the second plate 204 can have a closed-shape (e.g., a polygon, a rectangle, a square, a circle, an oval, a triangle, a pentagon, a hexagon, an octagon) or another suitable shape. For example, the second plate 204 and the base 210 may collectively form a T-shape, as viewed from above, when the second plate 204 lacks the first end portion 214, the second end portion 214, and the air gap 216.

Figure 4:
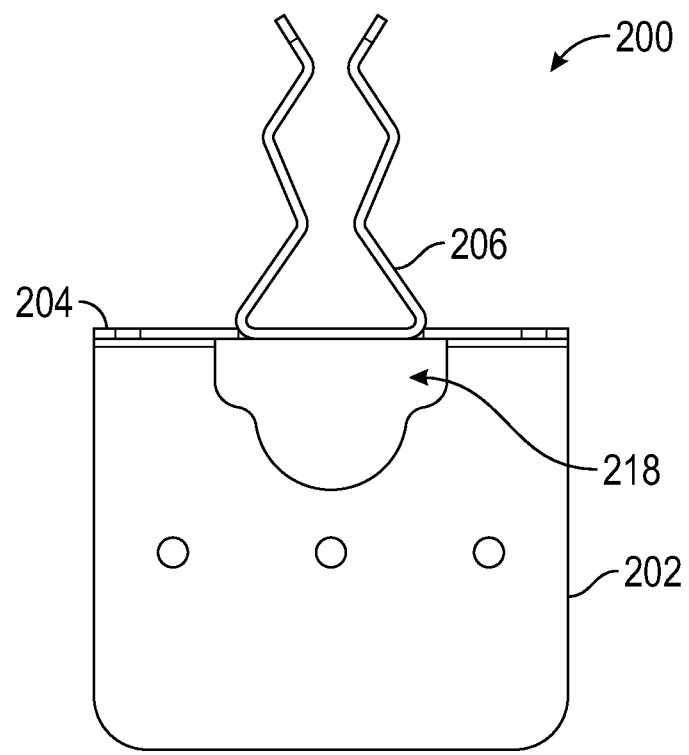
Figure 5:
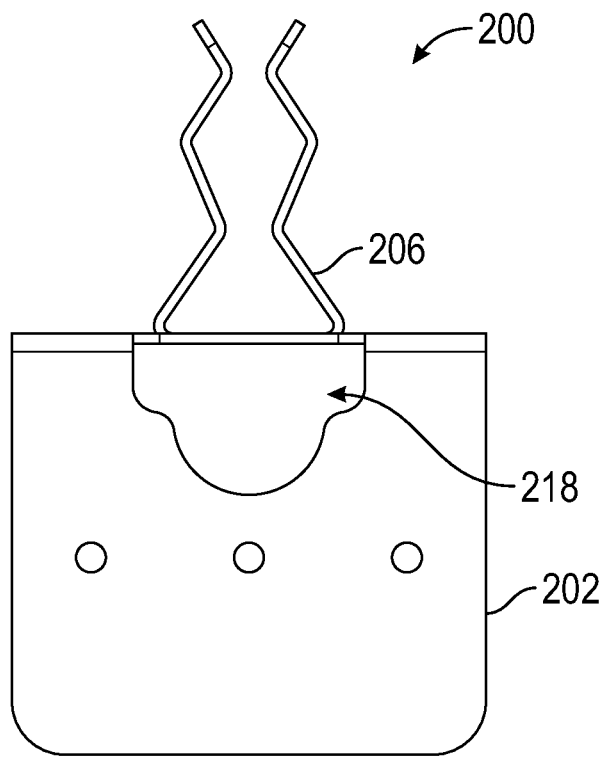

As shown in FIGS. 3-5, 8, and 9, the first plate 202 may define an opening 218 therethrough spanning between the first end portion 214 and the second end portion 214. As shown in FIG. 4 to FIG. 5, the first plate 202 defines the opening 218 along the first plane to have a first shoulder, a second shoulder, and a valley spanning between the first shoulder and the second shoulder, although this is not required and the opening 218 may lack the first shoulder, the second shoulder, or the valley.

The opening 218 may be immediately adjacent to the air gap 216, to be in fluid communication therewith, such that the opening 218 and the air gap 216 collectively enable the first plate 202 and the second plate 204 to collectively define a multi-plane opening extending along the first plane and the second plane, such that the second plate 204 extends between the multi-plane opening and the base 210, between the first end portion 214 and the second end portion 214. For example, as shown in FIG. 13, when the bracket 100 is used with multiple tubular members, there may be a first tubular member held by the clip 206 and a second tubular member extending through the opening 218, along the second plane, to enable the base 210 to extend between the first tubular member and the second tubular member when the first tubular member extends between the first finger 212 and the second finger 212. If the opening 218 and the air gap 216 collectively enable the first plate 202 and the second plate 204 to collectively define the multi-plane opening, then the first plate 202 defines the multi-plane opening along the first plane and the second plate 204 defines the multi-plane opening along the second plane. The second plate 204 may defines the multi-plane opening along the second plane by a portion that is wider than the base 210, although this configuration is not required (e.g., same width or smaller width).

The first plate 202 defines a set of bores 222 structured to receive a shank (e.g., a shaft) of a fastener (e.g., a bolt, a screw). Although the set of bores 222 includes three bores 222, this is not required and there can be less than three bores 222 (e.g., one or two) or more than three bores 222 (e.g., four, five). Each bore 222 in the set of bores 222 is internally smooth, but this configuration is not required and at least one bore 222 in the set of bores 222 can be threaded. One bore 222 of the set of bores 222 may be coaligned with the base 210, as shown in FIGS. 3-5. However, this is not required and other bores 222 (or no bores 222) in the set of bores 222 may be not coaligned with the base 210.

Figure 8:
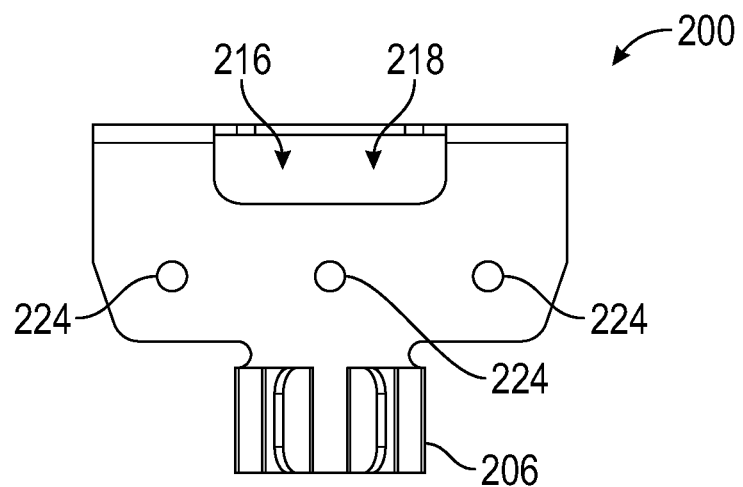
Figure 9:
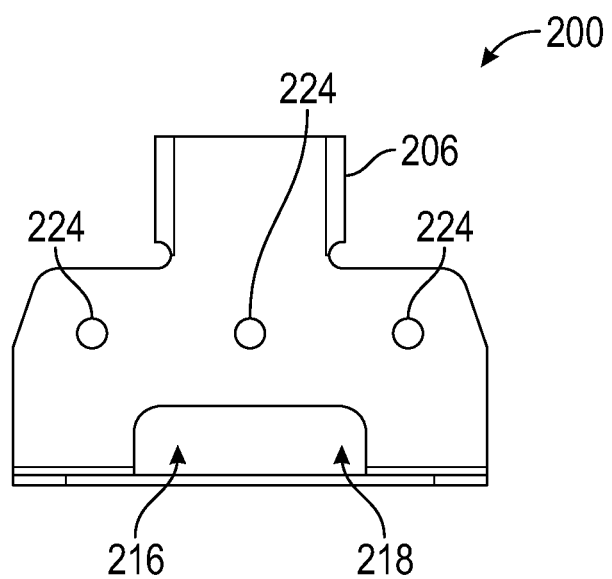
Figure 10:
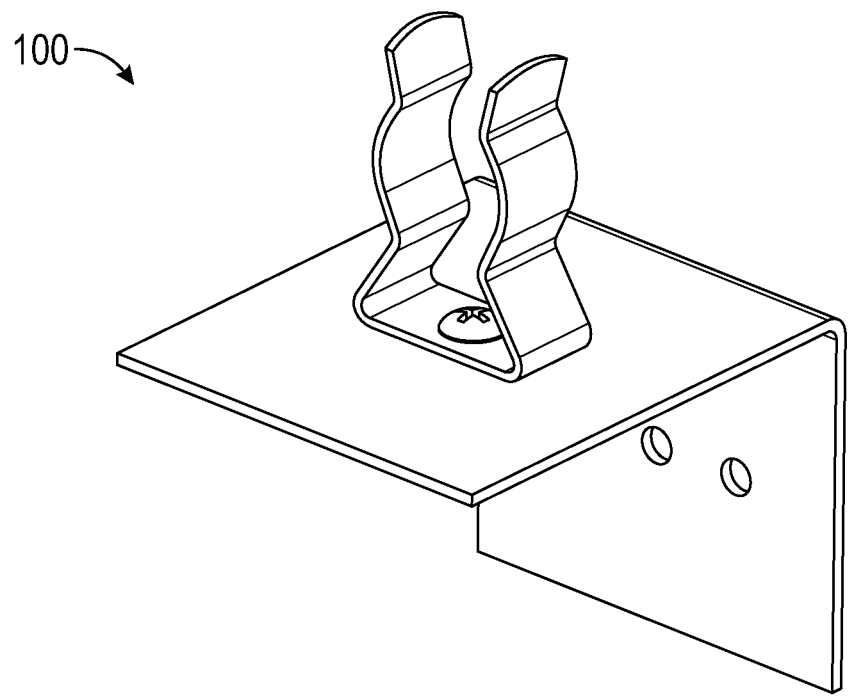
FIG. 10 shows the bracket of FIG. 1 to FIG. 2
Figure 11:
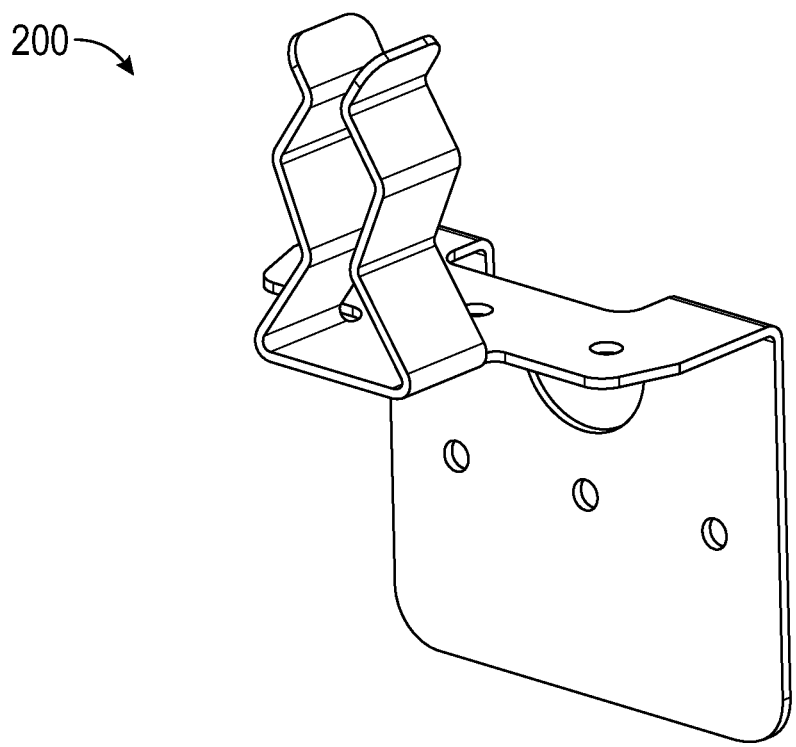
FIG. 11 shows the bracket of FIG. 3 to FIG. 9 according to this disclosure.

The second plate 204 defines a set of bores 224 structured to receive a shank (e.g., a shaft) of a fastener (e.g., a bolt, a screw). Although the set of bores 224 includes three bores 224, this is not required and there can be less than three bores 224 (e.g., one or two) or more than three bores 224 (e.g., four, five). Each bore 224 in the set of bores 224 is internally smooth, but this configuration is not required and at least one bore 224 in the set of bores 224 can be threaded. One bore 224 of the set of bores 224 may be coaligned with the base 210, as shown in FIGS. 3, 8, and 9. However, this is not required and other bores 224 (or no bores 224) in the set of bores 224 may be not coaligned with the base 210. Although the set of bores 222 is coaligned with the set of bores 224, this configuration is not required.

Figure 17:
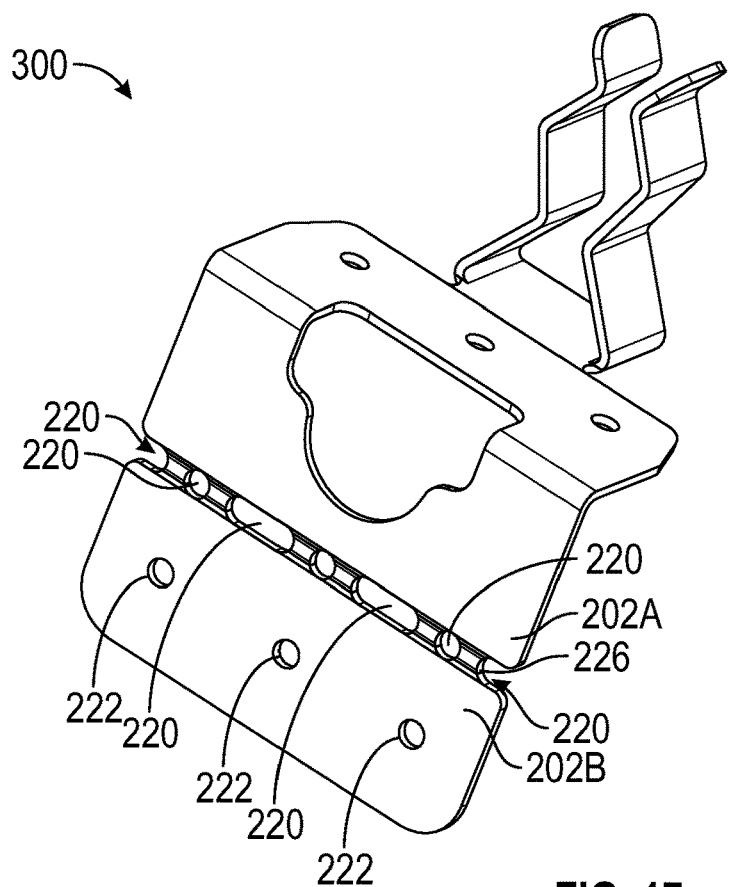
FIG. 17 to FIG. 18 show an embodiment of a bracket according to this disclosure.
Figure 18:
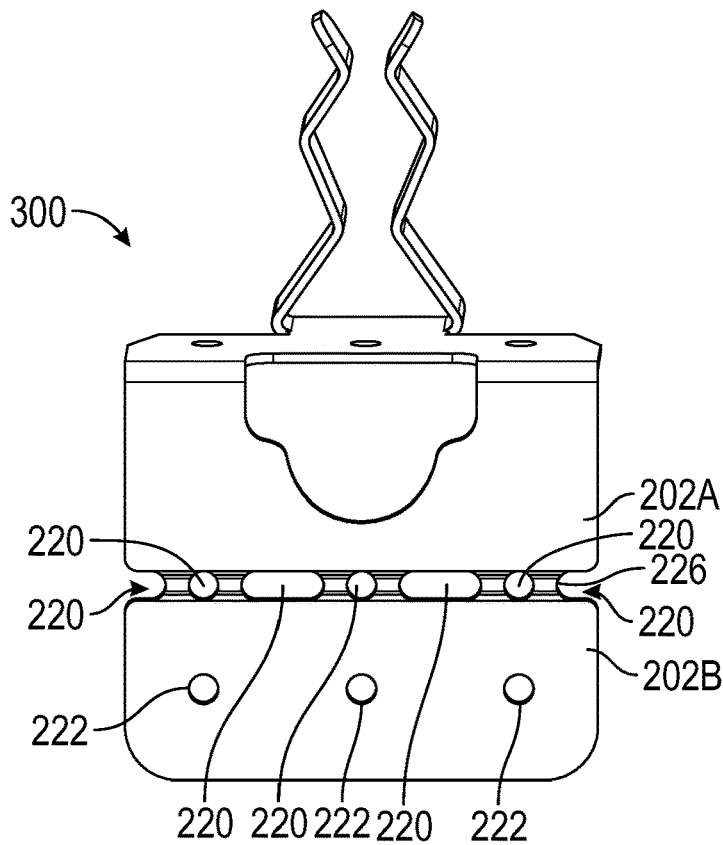

FIG. 17 to FIG. 18 show an embodiment of a bracket according to this disclosure. In particular, a bracket 300 is similar to the bracket 200, other than how the first plate 202 is configured. Specifically, the first plate 202 includes a first portion 202A and a second portion 202B, which are similarly shaped, sized, and constituted, although this configuration is not required and variations in shape, size, or constituency are possible, whether larger or smaller, whether of same or different constituency. The bracket 300 further includes a set of bridges 226 spanning between the first portion 202A and the second portion, to enable bending of the second portion 202B relative to the first portion 202A (or vice versa). The set of bridges 226 is monolithic with the first portion 202A and the second portion 202B, although this configuration is not required and the set of bridges 226 can be assembled (e.g., fastening, mating, adhering, magnetizing) with the first portion 202A or the second portion 202B. Likewise, although the set of bridges 226 includes six bridges 226, this configuration is not required and the set of bridges 226 can include less than six bridges 226 (e.g., five, four, three, two, one) or more than six bridges 226 (e.g., seven, eight, nine). The set of bridges 226 may be omitted.

The first portion 202A, the second portion 202B, and the set of bridges 226 collectively define a set of bores 220 through the first plate 202 about which the second portion 202B is bendable relative to the first portion 202A, where the set of bridges 226 may operate as a living hinge. The set of bores 220 includes bores that have a closed-shape (e.g., a circle, an oval) and an open-shape (e.g., a U-shape, a C-shape, a V-shape). The first portion 202A may have a first row of bores 220 and a second row of bores 220, where the first row of bores 220 is parallel to the second row of bores 220, and where each bore 220 in the first row of bores 220 and the second row of bores 220 is structured to receive a shank (e.g., a shaft) of a fastener (e.g., a bolt, a screw). For example, the first plate 202 and the second plate 204 may collectively define the multi-plane opening extending along the first plane and the second plane such that the second plate 204 extends between the multi-plane opening and the base 210. The first portion 202A and the second portion 202B may collectively define at least one bore 220 through the first plate 202 about which the second portion 202B is bendable relative to the first portion 202A, where that bore 220 extends between the multi-plane opening and the second portion 202B. The first portion 202A defines the multi-plane opening. The second portion 202B does not define the multi-plane opening.

The second portion 202B can be bendable relative to the first portion 202A to avoid facing the second plate 204. For example, the second portion 202B can be bendable relative to the first portion 202A to avoid facing the second plate 204 such that the second plate 204, the first portion 202A, and the second portion 202B form a Z-shape. The second portion 202B can be bendable relative to the first portion 202A to face the second plate 204. For example, the second portion 202B can be bendable relative to the first portion 202A to face the second plate 204 such that the second plate 204, the first portion 202A, and the second portion 202B form a C-shape or a U-shape. The second portion 202B can host the set of bores 222, although this configuration is not required and the first portion 202A can host the set of bores 222 or the set of bores 222 can be omitted from the first portion 202A or the second portion 202B. In some situations, the second portion 202B can be broken off from the set of bridges 226 or the first portion 202A, although this configuration is not required.

Figure 12:
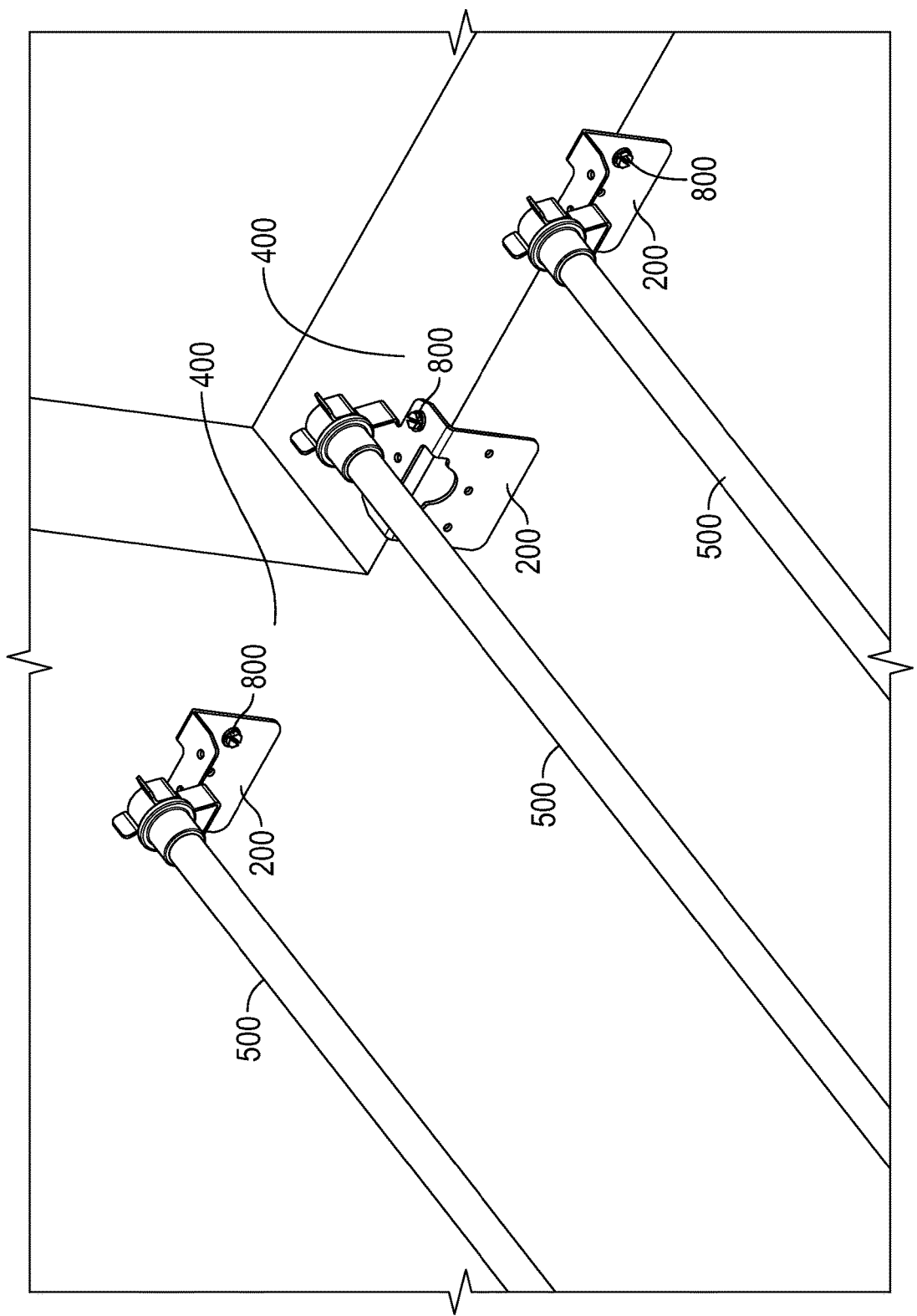
FIG. 12 shows how the bracket of FIG. 3 to FIG. 9 can be used with a tubular member and be secured to a surface of an object according to this disclosure.

FIG. 12 shows how the bracket of FIG. 3 to FIG. 9 can be used with a tubular member and be secured to a surface of an object according to this disclosure. In particular, the first plate 202 or the second plate 204 can be fastened to a surface 400 (e.g., a wall) of an object (e.g., an air handler) via a fastener 800 (e.g., a bolt, a screw) respectfully extending through the bore 222 or the bore 224. The clip 206 holds (e.g., clamps) a tubular member 500 (e.g., a tube, a bulb) by the first finger 212 and the second finger 212, while the tubular member 500 extends between the first finger 212 and the second finger 212. The tubular member 500 can extend toward or over the surface 400 or avoid extending toward or over the surface 400. Note that the bracket 300 may also be used this way. For example, the bulb may include a gas-discharge bulb, a fluorescent bulb, or any other suitable bulb. For example, the tube may include a conduit for conveying a fluid (e.g., a liquid, a gas), a solid beam, or another suitable tubular member.

Figure 13A:
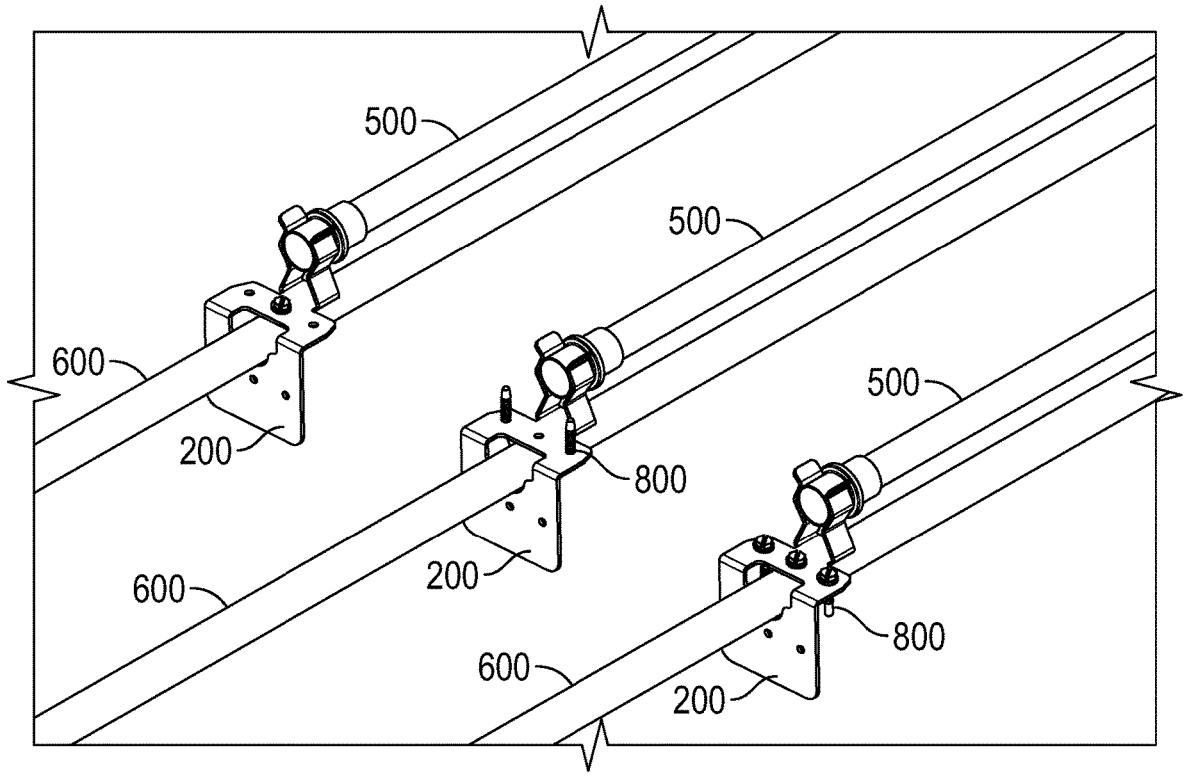
FIG. 13A to FIG. 13B show how the bracket of FIG. 3 to FIG. 9 can be used with a first tubular member, a second tubular member, and a strap according to this disclosure.
Figure 13B:
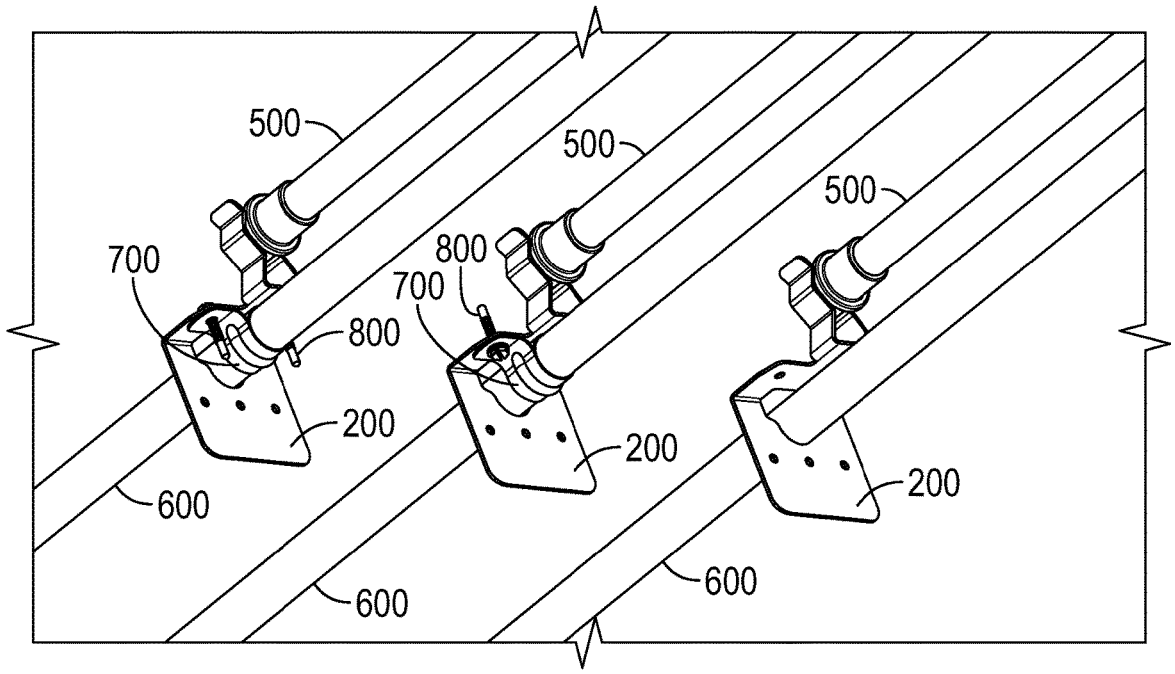

FIG. 13A to FIG. 13B show how the bracket of FIG. 3 to FIG. 9 can be used with a first tubular member, a second tubular member, and a strap according to this disclosure. In particular, there is a strap 700 (e.g., a U-shape, a C-shape) extending from the second plate 204, while exposed to the first plate 202, including the opening 218, such that the strap 700 avoids facing the first finger 212 and the second finger 212 or avoids underlay with the base 210. For example, the strap 700 can extend from the second plate 204 such that the strap 700 is exposed to the first plate 202 and not exposed to the first finger 212 and the second finger 212. The strap 700 can be fastened to the second plate 204 via the fasteners 800 extending through the set of bores 224.

The clip 216 holds the tubular member 500 by the first finger 212 and the second finger 212 as the tubular member 500 extends between the first finger 212 and the second finger 212. The opening 218 enables a second tubular member 600 to extend therethrough, while extending through the strap 700, such that the second tubular member 600 extends along the second plane or the second plate 204 or along the first tubular member 500 or parallel to the first tubular member 500. The second tubular member 600 can extend between at least two fasteners 800 or one fastener 800 can extend into the second tubular member 600 while being coaligned with the base 210.

Figure 14A:
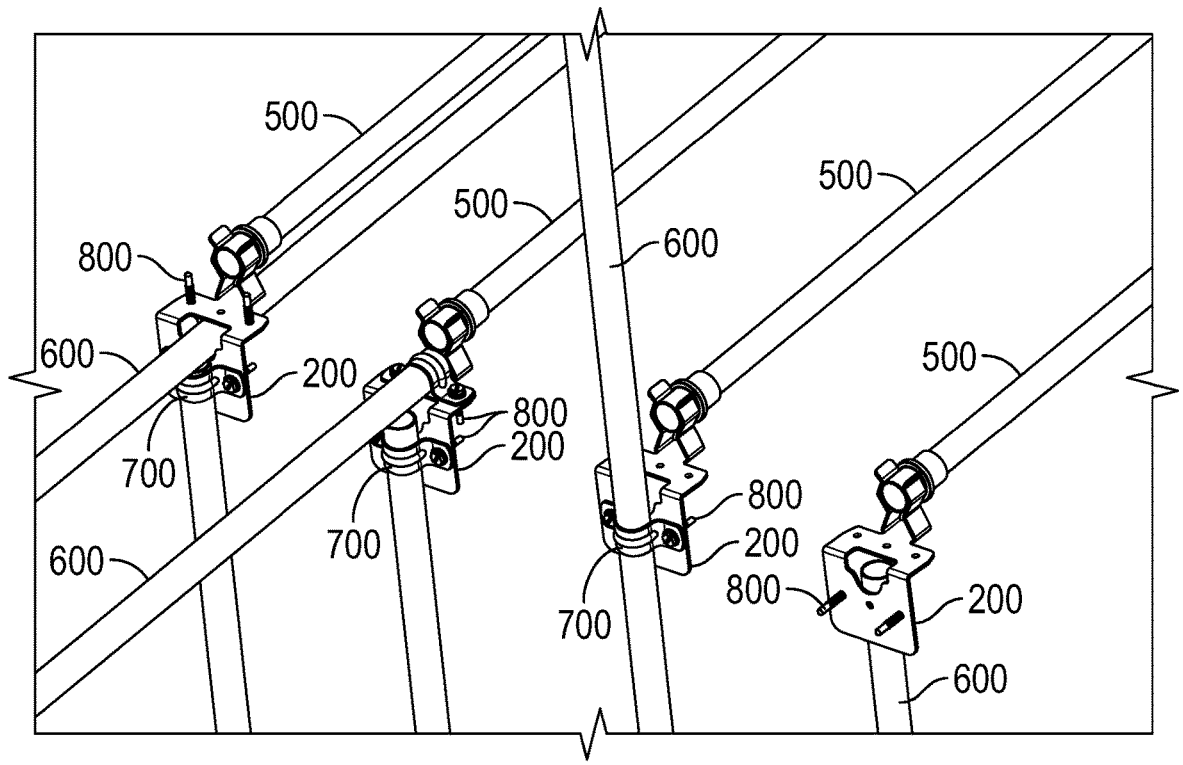
FIG. 14A to FIG. 14B show how the bracket of FIG. 3 to FIG. 9 can be used with a first tubular member, a second tubular member, and a strap according to this disclosure.
Figure 14B:
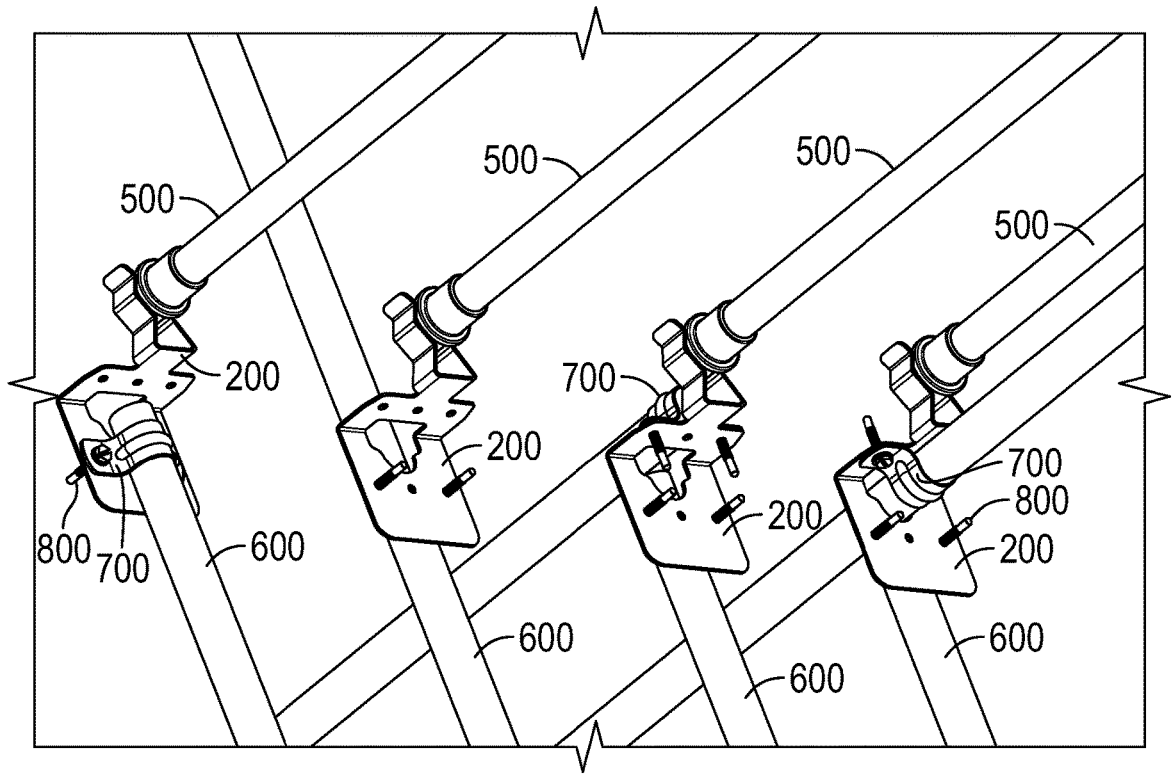

FIG. 14A to FIG. 14B show how the bracket of FIG. 3 to FIG. 9 can be used with a first tubular member, a second tubular member, and a strap according to this disclosure. In particular, the strap 700 extends from the first plate 202, which can be while avoiding underlay with the second plate 204 or while underlaying the second plate 204. The strap 700 can be fastened to the first plate 202 via the fasteners 800 through the set of bores 202. The second tubular member 600 can extend through the strap 700, whether extending past the strap 700 or not past the strap 700. The clip 500 holds (e.g., clamps) the first tubular member 500 by the first finger 212 and the second finger 212, while the tubular member 500 extends between the first finger 212 and the second finger 212. The second tubular member 500 can contact or avoid contact with the first tubular member 500 or the second plate 204. The strap 700 can extend from the second plate 204 such that the strap 700 is not exposed to the first plate 202 and exposed to the first finger 212 and the second finger 212.

Figure 15A:
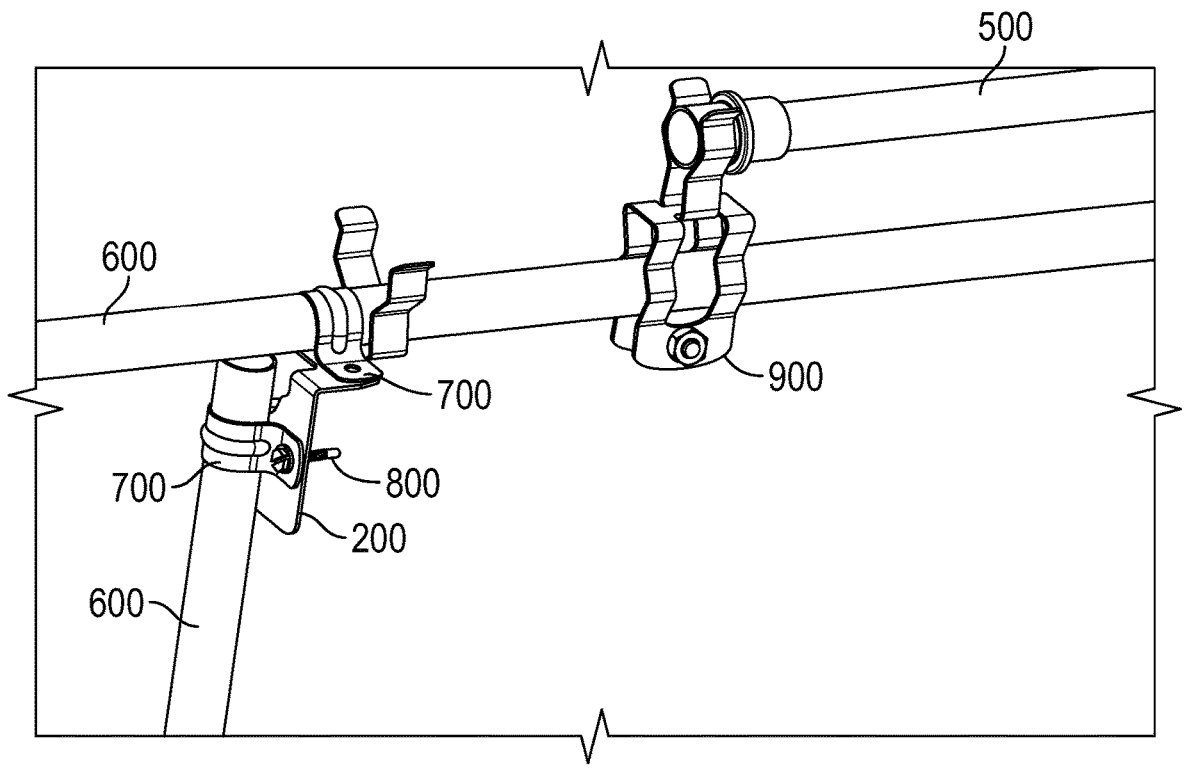
FIG. 15A to FIG. 15B show how the bracket of FIG. 3 to FIG. 9 can be used with a first tubular member, a second tubular member, and a strap according to this disclosure.
Figure 15B:
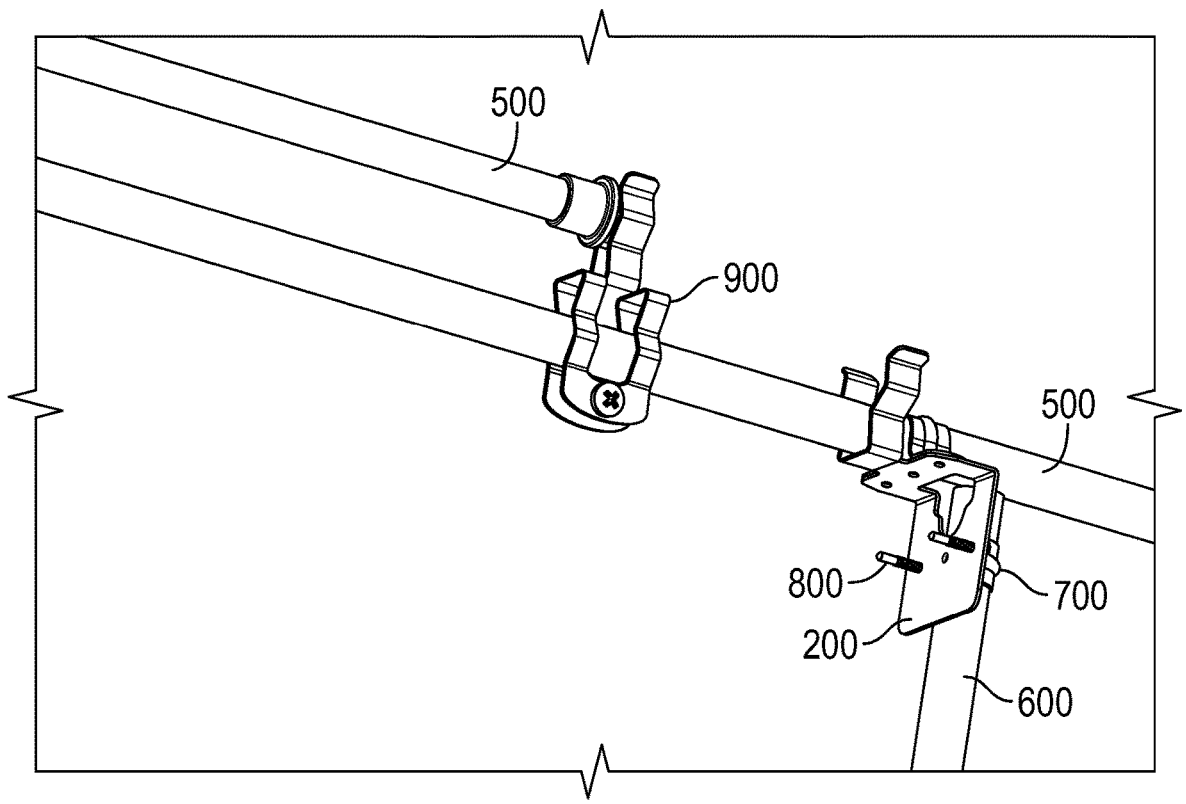

FIG. 15A to FIG. 15B show how the bracket of FIG. 3 to FIG. 9 can be used with a first tubular member, a second tubular member, and a strap according to this disclosure. In particular, there can be two straps 700 where one strap 700 extends from the second plate 204, while the clip 206 holds (e.g., clamps) the second tubular member 600 by the first finger 212 and the second finger 212 as the tubular member 600 extends between the first finger 212 and the second finger 212. Unlike FIGS. 12-14B where clip 206 held the tubular member 500 or 600 extending within an upper portion of an area between the first finger 212 and the second finger 212, this configuration shows the tubular member 500 or 600 extending within a lower portion of the area between the first finger 212 and the second finger 212. Likewise, note that a second bracket 900 may also clamp the second tubular member 600 while holding (e.g., clamping) another tubular member 500.

Figure 16A:
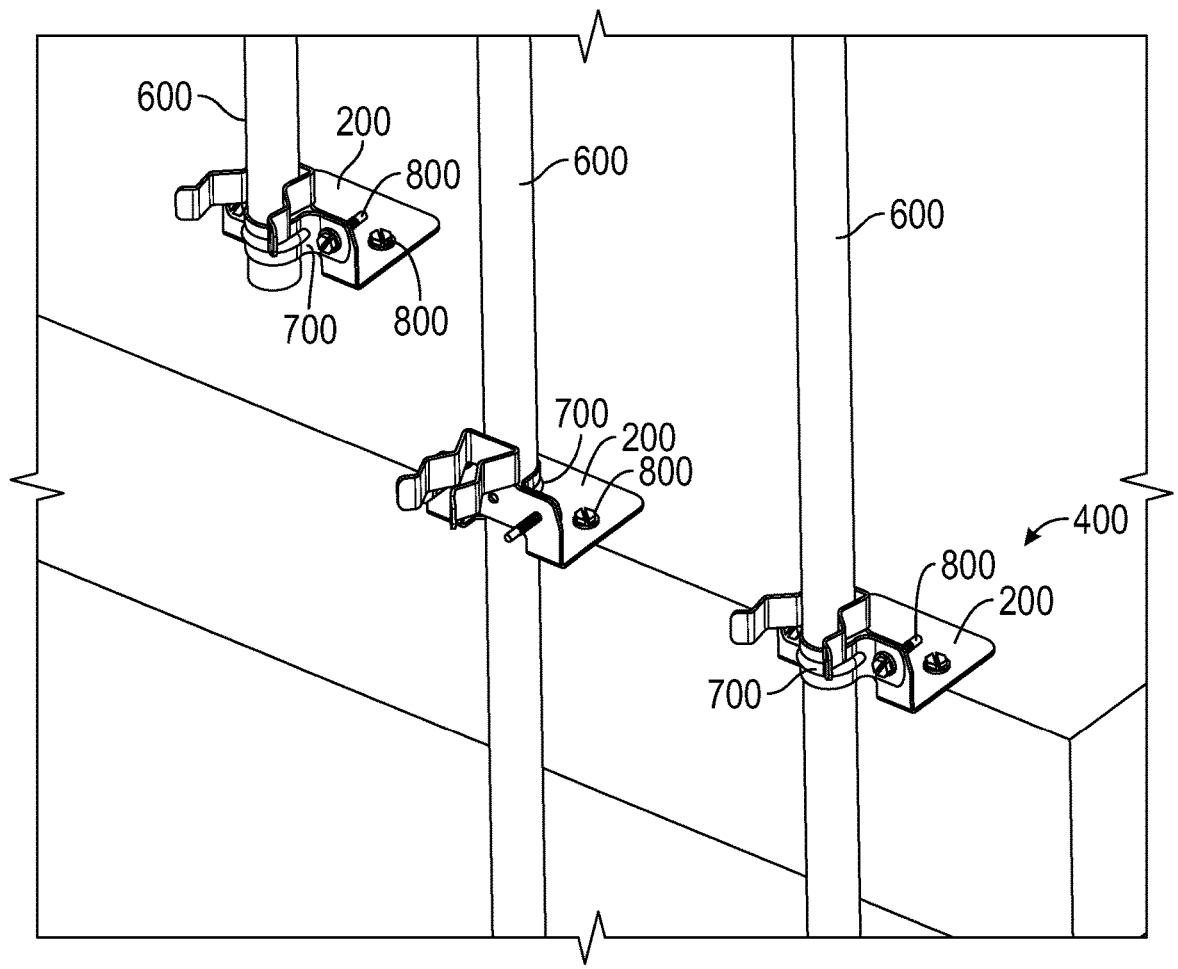
FIG. 16A to FIG. 16B show how the bracket of FIG. 3 to FIG. 9 can be used with a tubular member and a strap and be secured to a surface of an object according to this disclosure.
Figure 16B:
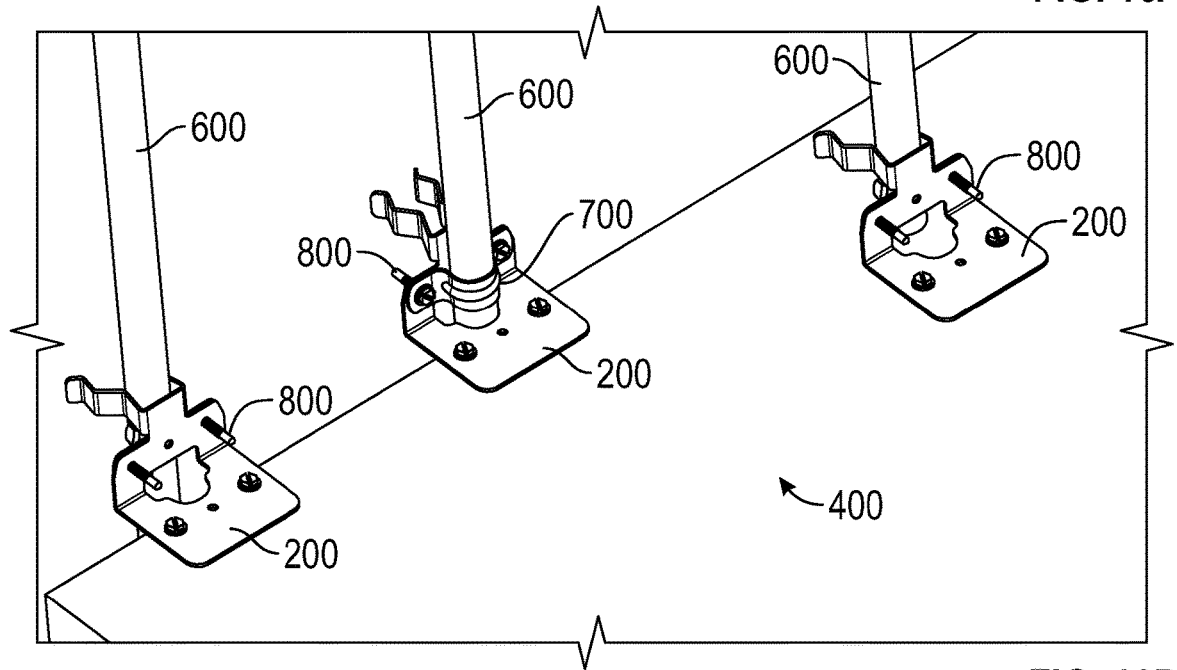

FIG. 16A to FIG. 16B show how the bracket of FIG. 3 to FIG. 9 can be used with a tubular member and a strap and be secured to a surface of an object according to this disclosure. In particular, the first plate 202 is secured to the surface 400 via the fasteners 800 extending through the set of bores 222. The strap 700 extends from the second plate 204, which can be while avoiding overlay over the first plate 202 or overlaying the first plate 202. The strap 700 is fastened to the second plate 204 via the fasteners 800 extending through the set of bores 224. Unlike FIGS. 12-14B where clip 206 held the tubular member 500 or 600 extending within the upper portion of the area between the first finger 212 and the second finger 212, this configuration shows the tubular member 500 or 600 extending within a lower portion of the area between the first finger 212 and the second finger 212.

Figure 19:
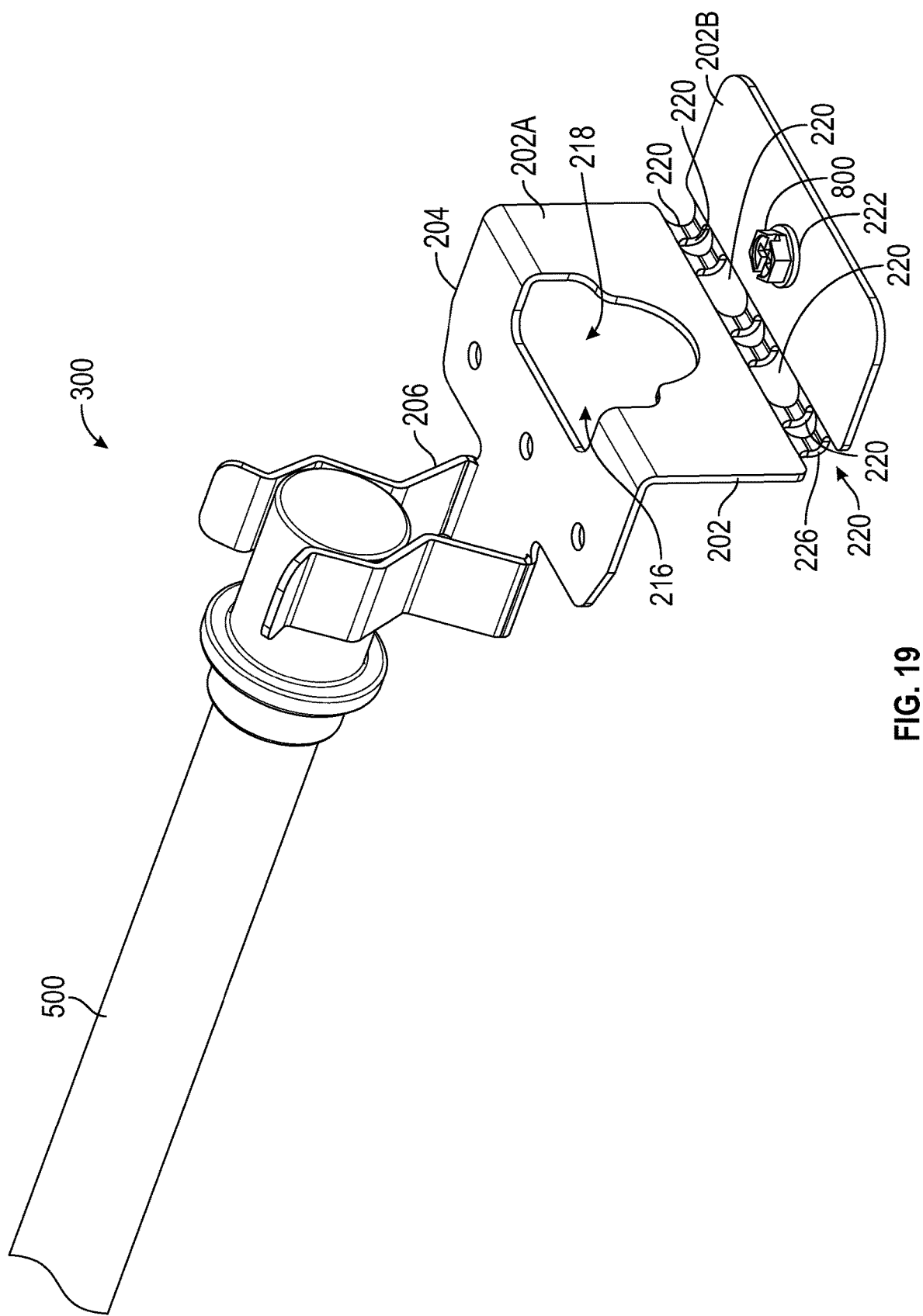
FIG. 19 shows how the bracket of FIG. 17 to FIG. 18 can be used with a tubular member according to this disclosure.

FIG. 19 shows how the bracket of FIG. 17 to FIG. 18 can be used with a tubular member according to this disclosure. In particular, the second portion 202B is bent (e.g., by hand) relative to the first portion 202A via the set of bridges 226, while the first portion 202A extends along the first plane, such that the second portion 202B can extend along the second plane, whether parallel or not parallel thereto. As shown, the second portion 202B avoids facing the second plate 204, which may enable the second plate 204, the first portion 202A, and the second portion 202B to form a Z-shape (e.g., depending on a degree of bend). However, the second portion 202B can face the second plate 204, which may enable the second plate 204, the first portion 202A, and the second portion 202B form a U-shape or a C-shape (e.g., depending on a degree of bend).

The bracket 200 or 300 can be sent to a user (e.g., via a courier, a governmental postal service), whether unpackaged or packaged in a package (e.g. a plastic bag, a sealed bag, a storage container, a cardboard box, a transport package, a consumer package, a bubble wrap, a foam blanket, a garment blanket, a can, a shrink-wrap, a molded pulp, a blister pack). There may be a set of instructions (e.g., a diagram, a photo, a user guide, a manual, a paper pamphlet, a sticker, a webpage, a video, an article, augmented reality wizard) associated with the bracket 200 or 300 and instructing the user how to operate the bracket 200 or 300, including any of its components. As such, the user can access the bracket 200 or 300 and operate the bracket 200 or 300 as instructed.

Although various embodiments have been depicted and described in detail herein, skilled artisans know that various modifications, additions, substitutions and the like can be made without departing from this disclosure. As such, these modifications, additions, substitutions and the like are considered to be within this disclosure.

What is claimed is:

1. A device, comprising:
a bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane such that the clip is able to hold a tubular member when the tubular member extends between the first finger and the second finger.

2. The device of claim 1, wherein the first finger and the second finger extend from the base away from the second plane such that the clip is able to hold the tubular member when the tubular member extends between the first finger and the second finger and not past the first plate.

3. The device of claim 1, wherein the first finger and the second finger extend from the base away from the second plane such that the clip is able to hold the tubular member when the tubular member extends between the first finger and the second finger and past the first plate.

4. The device of claim 1, wherein the second plate includes a first end portion and a second end portion spaced apart from each other to form an air gap therebetween such that the second plate has an open shape thereby as viewed from above when the first end portion and the second end portion extend from the first plate along the second plane.

5. The device of claim 4, wherein the first plate defines an opening therethrough spanning between the first end portion and the second end portion.

6. The device of claim 4, wherein the open shape is a first open shape, wherein the second plate and the base form a second open shape as viewed from above.

7. The device of claim 1, wherein the second plate has a portion, wherein the portion and the base form a T-shape as viewed from above.

8. The device of claim 1, wherein the second plate is wider than the base.

9. The device of claim 1, wherein the first plane and the second plane intersect at an angle of about 90 degrees.

10. The device of claim 1, wherein the second plate transitions to the base such that the second plate is flush with the base.

11. The device of claim 1, wherein the base is monolithic with the second plate.

12. The device of claim 10, wherein the second plate is monolithic with the first plate.

13. The device of claim 1, wherein the first plate includes a first portion and a second portion, wherein the first portion and the second portion collectively define an opening through the first plate about which the second portion is bendable relative to the first portion.

14. The device of claim 13, wherein the second portion is bendable to avoid facing the second plate.

15. The device of claim 13, wherein the second portion is bendable to face the second plate.

16. The device of claim 13, wherein the second portion defines a bore structured to receive a shank of a fastener.

17. The device of claim 1, wherein the first plate and the second plate collectively define an opening extending along the first plane and the second plane such that the second plate extends between the opening and the base.

18. The device of claim 17, wherein the opening is a first opening, wherein the first plate includes a first portion and a second portion, wherein the first portion and the second portion collectively define a second opening through the first plate about which the second portion is bendable relative to the first portion, wherein the second opening extends between the first opening and the second portion.

19. The device of claim 18, wherein the first portion defines the first opening.

20. The device of claim 18, wherein the second portion does not define the first opening.

21. The device of claim 1, wherein the first plate, the second plate, and the base define an L-shape.

22. The device of claim 1, wherein the second plate defines a bore structured to receive a shank of a fastener.

23. The device of claim 22, wherein the bore is coaligned with the base.

24. The device of claim 22, wherein the bore is not coaligned with the base.

25. The device of claim 1, wherein the tubular member is a first tubular member, wherein the first plate defines an opening therethrough such that a second tubular member is able to extend through the opening along the second plane to enable the base to extend between the first tubular member and the second tubular member when the first tubular member extends between the first finger and the second finger.

26. The device of claim 25, wherein the first plate defines the opening along the first plane, wherein the second plate defines the opening along the second plane.

27. The device of claim 26, wherein the second plate defines the opening along the second plane by a portion that is wider than the base.

28. The device of claim 25, wherein the first plate defines the opening along the first plane to have a first shoulder, a second shoulder, and a valley spanning between the first shoulder and the second shoulder.

29. The device of claim 1, further comprising:
a strap extending from the second plate such that the strap avoids facing the first finger and the second finger.

30. The device of claim 1, further comprising:
a strap extending from the second plate such that the strap is exposed to the first plate and not exposed to the first finger and the second finger.

31. The device of claim 1, further comprising:
a strap extending from the second plate such that the strap is not exposed to the first plate and exposed to the first finger and the second finger.

32. The device of claim 1, wherein the first plate has a first row of bores and a second row of bores, wherein the first row of bores is parallel to the second row of bores, wherein each bore in the first row of bores and the second row of bores is structured to receive a shank of a fastener.

33. The device of claim 1, wherein the first plate has a pair of oval bores.

34. The device of claim 1, wherein the tubular member includes a gas-discharge bulb or a conduit.

35. A method, comprising:
sending a bracket to a user, wherein the bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane; and
instructing the user to operate the clip such that the clip holds a tubular member as the tubular member extends between the first finger and the second finger.

36. A method, comprising:
causing a bracket to be accessed, wherein the bracket includes a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane; and
causing the clip to hold a tubular member as the tubular member extends between the first finger and the second finger.

37. A method, comprising:
manufacturing a bracket including a first plate, a second plate, and a clip, wherein the first plate extends along a first plane, wherein the second plate extends from the first plate along a second plane away from the first plane, wherein the first plane intersects the second plane, wherein the second plate includes an end section distal to the first plate, wherein the clip includes a base, a first finger, and a second finger, wherein the base extends from the end section along the second plane away from the first plane, wherein the first finger and the second finger extend from the base away from the second plane such that the clip is able to hold a tubular member when the tubular member extends between the first finger and the second finger.

38. The device of claim 7, wherein the second plate and the base form a Y-shape as viewed from above.

39. The device of claim 1, wherein the second plate and the base form a Y-shape as viewed from above.

* * * * *

UNITED STATES PATENT AND TRADEMARK OFFICE
CERTIFICATE OF CORRECTION

PATENT NO. : 12,007,052 B2
APPLICATION NO. : 18/098640
DATED : June 11, 2024
INVENTOR(S) : Thomas Wouters et al.

It is certified that error appears in the above-identified patent and that said Letters Patent is hereby corrected as shown below:

On the Title Page

Column 1 Item (63) Related U.S. Application Data should read:
(63) Continuation-in-part of application No. 17/300,323, filed on Jul. 15, 2022, and is a continuation-in-part of application No. 17/300,324, filed on Jan. 19, 2022.

Signed and Sealed this
Twenty-fourth Day of September, 2024

Katherine Kelly Vidal
*Director of the United States Patent and Trademark Office*